US00PP28701P3

(12) United States Plant Patent
Hansen

(10) Patent No.: US PP28,701 P3
(45) Date of Patent: Nov. 28, 2017

(54) ***ALLIUM* PLANT NAMED 'MEDUSA'**

(50) Latin Name: ***Allium* hybrid (Linnaeus)**
Varietal Denomination: Medusa

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 25 days.

(21) Appl. No.: 14/998,558

(22) Filed: Jan. 19, 2016

(65) Prior Publication Data

US 2017/0208721 P1 Jul. 20, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

UPOV Record Detail, Takii Mar. 28, 2014.*
UPOV Record Detail, Agromar Oct. 26, 2015.*

* cited by examiner

*Primary Examiner* — Keith O Robinson

(57) ABSTRACT

A new and distinct cultivar of ornamental onion plant named *Allium* 'Medusa' compact habit, glaucous, upright, stiff, strap-like, flattened, gray-green foliage with longitudinal twisting and numerous, tightly-clustered, purple flowers forming long-blooming globose umbels and scapes that typically begin development pointing toward the ground.

1 Drawing Sheet

Botanical classification: *Allium* hybrid (Linnaeus).
Variety denomination: 'Medusa'.

BACKGROUND AND ORIGIN OF THE PLANT

The present invention relates to the new and distinct ornamental onion, *Allium* 'Medusa' developed and discovered by the inventor at a private garden in Waseca, Minn., USA as the result of a chance cross between a proprietary unreleased selection (not patented) of *Allium senenscens* subspecies *glaucum* as the female parent and a proprietary unreleased selection (not patented) of *Allium tanguticum* as the male parent. The plant was originally discovered by the inventor in the summer of 2008. *Allium* 'Medusa' has been successfully asexually propagated by garden bulb division method since 2009 at a wholesale perennial nursery in Zeeland, Mich. and found to be stable and produce identical plants that maintain the unique characteristics of the original plant through multiple generations.

No plants of *Allium* 'Medusa' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE PLANT

*Allium* 'Medusa' differs from its parents as well as all other ornamental onion known to the applicant. The most similar known *Allium* cultivars are *Allium senenscens* 'Blue Eddy' (not patented), *Allium tanguticum* 'Summer Beauty' (not patented), 'Back to School' (not patented), 'Millenium'

(not patented) and 'Noneuq' U.S. Plant Pat. No. 22,115. 'Blue Eddy' has a shorter leaves, flowers and overall habit and smaller flower globes and lighter colored flowers. 'Summer Beauty' is larger in habit, with less-twisted leaves and lighter flowers in larger umbels. 'Back to School' is shorter in habit, flowers later in the season and has foliage that does not last as long in the season. 'Millenium' has broader foliage with less twisting, larger habit and larger umbels of lighter purple. 'Noneuq' is more commonly known as 'Balloon Banquet' and is earlier blooming, shorter umbels and fewer flowers per inflorescence.

The female parent has broader and more twisted foliage than the new plant, and the male parent has taller and thinner foliage than the new plant.

*Allium* 'Medusa' differs from these above cultivars and all unregistered cultivars known to the inventor in that it has:

1. Glaucous, upright, stiff, strap-like, flattened, gray-green foliage with longitudinal twisting.
2. Compact habit, drought tolerant, rabbit and deer resistant, medium-sized clumps.
3. Numerous, tightly-clustered, purple flowers forming long-blooming globose umbel.
4. Young peduncles inverted and becoming upright to slightly curved in maturity.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
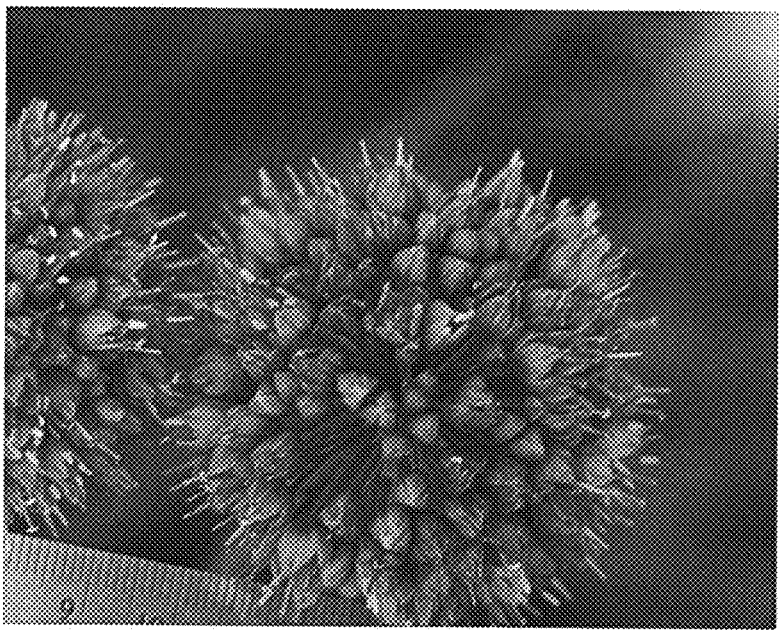
FIG. 1 shows a close-up of the umbel.
Figure 2:
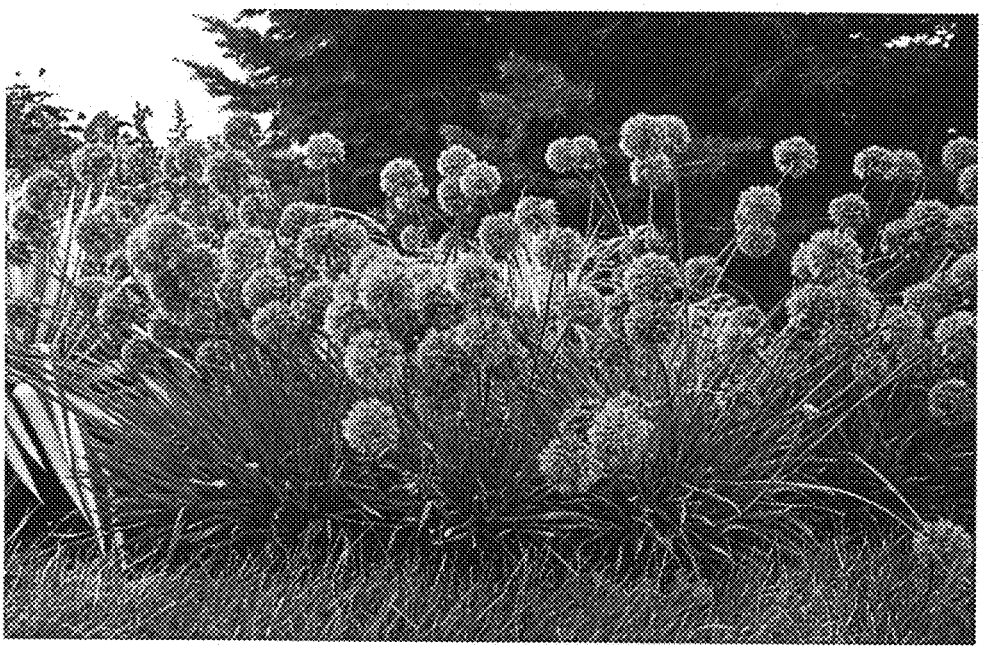
FIG. 2 shows the side-view habit of a two-year-old plant in midseason.

The following descriptions and color references are based on The 2001 edition of The Royal Horticultural Society Colour Chart except where common dictionary terms are used. The new plant, *Allium* 'Medusa', has not been observed under all possible environments. The phenotype may vary slightly with different environmental conditions, such as temperature, light, fertility, moisture and maturity levels, but without any change in the genotype. The following observations and size descriptions are of a three-year-old plant in a trial garden of a wholesale perennial nursery in Zeeland, Mich. under full sun with supplemental water and fertilizer as needed.

Botanical classification: *Allium* hybrid.

Parentage: Proprietary unreleased selection of *Allium senenscens* subspecies *glaucum* (not patented) as the female or seed parent and *Allium tanguticum* as the male or pollen parent.

Propagation method: By garden bulb division.

Growth rate: Vigorous, flowering in 4 liter containers in about 12 weeks.

Rooting habit: Fibrous from base of bulbs, lightly branching; color nearest RHS 158C.

Plant habit description: Dense clump of bulbs with sessile rosulate foliage about 55.0 cm across and about 28.0 cm tall; flowering to about 55.0 cm tall.

Bulbs: Elongated conical shape; about 4.5 cm long and 1.0 cm diameter at base; about 85 per plant; color nearest RHS 155D.

Leaves: Sessile; linear; glaucous, glabrous dull surfaces; semi-succulent; simple, margin entire; sharply acute apex, truncate base; twisted longitudinally 360° to 450°; slightly concavo-convex; about 24.0 cm long and about 7.0 mm diameter at base; arranged in two-ranked tuffs from bulb; fragrance onion-scented.

Leaf color: Mature and expanding leaves same; both surfaces between RHS 137A and RHS 137B distally with base nearest RHS 146D.

Leaf venation: Parallel; color same as leaf abaxial and adaxial.

Inflorescence: In terminal umbel; about 234 to 312 flowers per inflorescence; about 60 to 70 inflorescences per plant; slightly flattened globe, about 5.5 cm across and about 4.5 cm tall; lasting about four weeks; onion-like fragrance; beginning in mid-August in Michigan and continuing for five to six weeks.

Blooming habit: With slightly flattened drooping globe in bud, becoming upright as initial flowers open; one terminal umbel inflorescence per stem.

Flowers: Campanulate; incomplete, with two sets of three tepals, outer set smaller than inner; inferior ovary; actinomorphic; upward and outwardly facing depending on position in umbel; individually effective about four to six days; from base to exerted stamens to about 10.0 mm long and about 7.0 mm across.

Tepals (outer set): Convex; glabrous; acute apex, truncate base; about 5.0 mm long and about 2.0 m across.

Tepal (inner set): Flat; glabrous; acute apex, broadly acute base; about 6.0 mm long and about 3.0 mm across.

Tepal color (outer set): Abaxial and adaxial apex nearest RHS 77A, both surfaces lightening to between RHS 77B and RHS 77C at base.

Tepal color (inner set): Abaxial and adaxial nearest RHS 77B.

Buds one day prior to opening: Conical, slightly flattened on three sides; rounded base, acute apex; about 7.0 mm long and about 4.0 mm diameter at widest point.

Bud color: Nearest RHS 77A at petal apex and lightening to nearest RHS 77B in middle and nearest RHS 77C at base.

Pedicel: Terete; stiff, upward and outwardly facing depending on orientation in umbel; glabrous; glaucous; about 15.0 mm long and about 0.5 mm diameter.

Pedicel color: Between RHS 138A and RHS 138B.

Peduncle: Glabrous, glaucous; flattened trapezoid in cross-section; about 49 cm long and base about 7.5 mm wide at thicker side and about 5.0 mm on narrower side; as immature inflorescence pointing downward, becoming erect to slightly curving near top when in flower; prior to all flowers opening distal 3.0 to 5.0 cm curled downward 180° from vertical.

Peduncle color: Between RHS 137A and RHS 137B.

Gynoecium: Pistil single; to about 8.0 mm long.

*Style*.—Single, cylindrical, glabrous, about 2.0 expanding to 4.5 mm long and about 0.5 mm across when mature; color nearest RHS 77C.

*Stigma*.—Globose; about 0.4 mm across; color lighter than RHS 77D.

*Ovary*.—Distinctly tri-carpeled; obcordate, widest at apex and narrowest at base; about 3.0 mm long and 2.0 mm across at apex and 1.0 mm across at base; color nearest RHS 77B at apex and nearest RHS 77C at base.

Androecium: Five; to about 8.7 mm long.

*Anther*.—Oblong; about 1.7 mm long and about 0.7 mm wide; dorsifixed; longitudinal; color nearest RHS 186C.

*Filament*.—Exserted; glabrous; about 7.0 mm long and 1.0 mm at base; color nearest RHS 77A at apex and lightening to nearest RHS 77C at base.

*Pollen*.—Abundant; color nearest RHS 160C.

Fruit: Tri-valved loculicidal capsule; about 4.0 mm long and 3.0 mm across; typically dehiscing to within about 1.0 mm of base; one to three seeded; color upon maturity nearest RHS 199D.

Seed: Elliptic, flattened along one long side; about 2.5 mm long and about 1.5 mm across; color nearest RHS 202A.

Disease and pest resistance: Ornamental onions typically resist deer and rabbit feeding. Resistance beyond that of other ornamental onion has not been observed. The plant grows best with good drainage and is able to tolerate some drought when established. Hardiness at least from USDA zone 4 through 8.

I claim:

1. A new and distinct cultivar of ornamental onion plant named *Allium* 'Medusa' as herein described and illustrated, suitable as a potted plant, for the garden, and for cut flower arrangements.

* * * * *